US005689833A

United States Patent [19]

Allen et al.

[11] Patent Number: 5,689,833

[45] Date of Patent: Nov. 25, 1997

[54] EYE SHIELD FOR A RESPIRATORY MASK

[75] Inventors: Peter B. Allen, Bracknel; David Cook, Durham, both of United Kingdom; William A. Mittelstadt, Woodbury, Minn.

[73] Assignee: Minnesota Mining and Manufacturing Company, St. Paul, Minn.

[21] Appl. No.: 433,808

[22] Filed: May 3, 1995

[51] Int. Cl.[6] .............................. A61F 9/02; A62B 18/02

[52] U.S. Cl. .......................... 2/427; 128/201.15; 128/857

[58] Field of Search .................................. 2/426, 427, 9, 2/206; 128/206.21, 206.28, 201.15, 205.25, 206.12, 206.15, 207.12, 206.19, 207.11, 857, 858, 863, 206.23

[56] References Cited

U.S. PATENT DOCUMENTS

| | | | |
|---|---|---|---|
| 2,435,653 | 2/1948 | Maurer | 128/210.15 |
| 2,462,005 | 9/1949 | Schauwecker | 128/146 |
| 2,740,400 | 4/1956 | Wines | 128/146 |
| 2,762,368 | 1/1956 | Bloomfield | 128/146 |
| 3,232,290 | 2/1966 | Nicolai | 128/141 |
| 3,528,415 | 9/1970 | Malmin | 128/142.6 |
| 3,563,236 | 2/1971 | Hansson | 128/201.15 |
| 3,602,219 | 8/1971 | Warncke | 128/201.15 |
| 3,680,555 | 8/1972 | Warneke | 128/141 |
| 3,747,599 | 7/1973 | Malmin | 128/142.7 |
| 3,971,368 | 7/1976 | Forbes et al. | 128/142 |
| 4,069,516 | 1/1978 | Watkins, Jr. | 2/428 |
| 4,126,131 | 11/1978 | Davis et al. | 128/142.4 |
| 4,404,969 | 9/1983 | Cresswell et al. | 128/201.23 |
| 4,534,344 | 8/1985 | Constance-Hughes | 128/201.15 |
| 4,676,236 | 6/1987 | Piorkowski et al. | 128/201.23 |
| 4,989,598 | 2/1991 | Berg et al. | 128/206.23 |
| 5,062,421 | 11/1991 | Burns et al. | 128/205.27 |
| 5,235,972 | 8/1993 | Strong | 128/206.21 |
| 5,263,477 | 11/1993 | Crome | 128/205.24 |
| 5,406,944 | 4/1995 | Gazzara | 128/857 X |

FOREIGN PATENT DOCUMENTS

| | | | |
|---|---|---|---|
| 2 637 808 | 4/1990 | France . | |
| 2 700 747 | 7/1994 | France . | |
| 26 43 853 | 3/1978 | Germany . | |
| 05 29 03921 | 8/1980 | Germany . | |
| 42 20 790 C1 | 9/1993 | Germany | A62B 18/08 |
| 2 008 413 | 8/1992 | United Kingdom . | |
| 2 228 420 | 7/1993 | United Kingdom . | |
| 2 249 963 | 1/1994 | United Kingdom . | |
| WO 95/20995 | 8/1995 | WIPO | A62B 18/08 |

*Primary Examiner*—Peter Nerbun
*Attorney, Agent, or Firm*—Gary L. Griswold; Walter N. Kirn; James A. Rogers

[57] ABSTRACT

A respiratory mask is provided with an eye shield having a body portion which is releasably-secured to the mask, and a shield portion which shields the eyes of the wearer. The shield portion is self-supporting on the body portion and, hence, on the mask, and includes a sheet of transparent, eye-shielding, material which can be replaced if it becomes marked or damaged. The shield portion can be pivoted forwards, relative to the mask, so that it is removed from the line of vision of the wearer without affecting the respiratory protection provided by the mask. A valve arrangement in the body portion of the eye shield can divert air from the mask into the shield portion, to remove contaminants from the region around the eyes of the wearer.

5 Claims, 10 Drawing Sheets

EYE SHIELD FOR A RESPIRATORY MASK

The present invention relates to respiratory masks, that is masks that will provide respiratory protection against contaminants, for example solid particles, mists, gases and vapours, in the air.

Respiratory masks are worn by people working in environments where toxic or noxious contaminants are present in the air. Paint spraying, for example, is an occupation that can generate such contaminants, making the use of respiratory masks highly desirable and usually essential. Some activities may also generate flying particles or droplets, or contaminants that can irritate the eyes, in which case it is important for workers to use some form of eye protection as well as respiratory protection.

Various forms of respiratory protection are available, some of which also provide protection for the eyes. A full face mask, for example, covers the wearer's entire face and will provide protection both for the eyes and the respiratory system, as will a hood or helmet that covers the wearer's entire head. A half or quarter mask, on the other hand, does not cover the eyes, and the wearer will be required to use some form of separate eye shield or goggles if the eyes need protection. However, eye shields and goggles are not always easy to fit or remove when a half or quarter mask is being worn. Moreover, while the protection offered by a simple eye shield or by goggles is quite adequate in certain circumstances, it is limited and would not generally be particularly effective against mists and vapours.

A paint spray worker encounters particular problems when using respiratory protection such as a full face mask (or a hood or helmet that covers the entire head) because the lens, or viewing window, tends to be splashed by paint which impairs the wearer's vision. It is possible to protect the lens by using a film cover which can be removed when it becomes obscured, and it is also known to provide a secondary lens over the primary lens for the same purpose. However, those arrangements do not generally improve the wearer's vision because the film cover or secondary lens can cause multiple reflections. Consequently, the wearer will often lift the respirator away from the face to obtain a better view of the work that is being carded out and, in doing so, loses not only eye protection but also respiratory protection at a time when contaminants are still present in the air.

It is known to circulate air inside a respiratory mask with a view to preventing the wearer's vision from being impaired by the formation of mist on the inside surface of the lens and, in some cases, that circulated air is subsequently passed into the breathing circuit of the mask. Such air circulation does not, of course, protect the outside surface of the lens from being marked during use The present invention provides an eye shield for use in combination with a respiratory mask which is adapted to fit to, and seal against, the face of a wearer, the eye shield comprising an eye-shielding portion, and attachment means by which the eye shield can be releasably-secured to the mask in positive engagement therewith and positioned to shield the eyes of a wearer without, in use, requiring means for securing the eye shield to the head of the wearer.

The present invention also provides a respiratory mask which is formed to fit to, and seal against, the face of a wearer to provide respiratory protection, the mask being in combination with an eye shield movable between a first position in which it is positioned to shield the eyes of a wearer and a second position in which it is removed from, and located below, the line vision of the wearer, wherein the respiratory protection afforded by the mask is unaffected by the position of the eye shield.

The present invention further provides a respiratory mask which is formed to fit to, and seal against, the face of a wearer to provide respiratory protection, and which includes an exhalation valve through which air leaves the mask, the mask being in combination with an eye shield to provide protection to the eyes of the wearer, and valve means having a diverter position in which the valve means diverts air that has passed through the exhalation valve to the interior of the eye shield.

In accordance with another aspect of the invention, there is provided a respiratory mask which is formed to fit to, and seal against, the face of a wearer to provide respiratory protection, the mask being in combination with an eye shield which comprises a frame shaped to extend across, and around the sides of, the face of a wearer and to enclose a sheet of eye-shielding material, wherein the sheet of eye-shielding material is a flat sheet and is removably-held in the frame.

In accordance with a still further aspect of the invention, there is provided a respiratory mask which is formed to fit to, and seal against, the face of a wearer to provide respiratory protection, the mask being in combination with an eye shield which is pivotally movable relative to the mask whereby the position of the eye shield relative to the face of a wearer can be adjusted, the eye shield including resilient means arranged to bias the eye shield in the direction of the face of the wearer.

By way of example only, embodiments of the invention will be described with reference to the accompanying drawings, in which.

Figure 1:
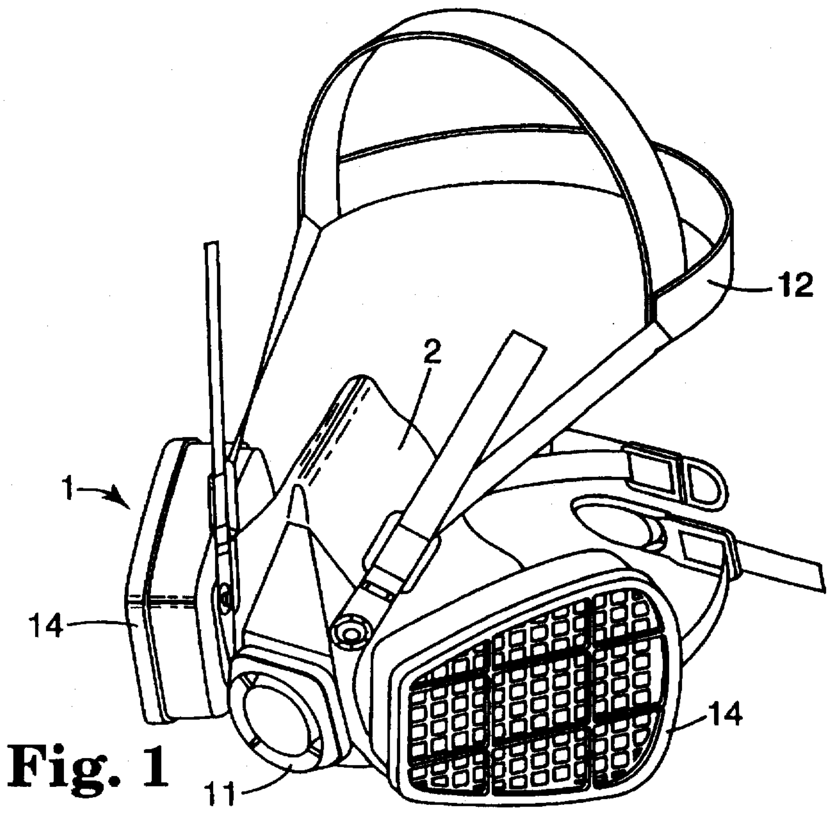
FIG. 1 is a perspective view of a respiratory mask.
Figure 2:
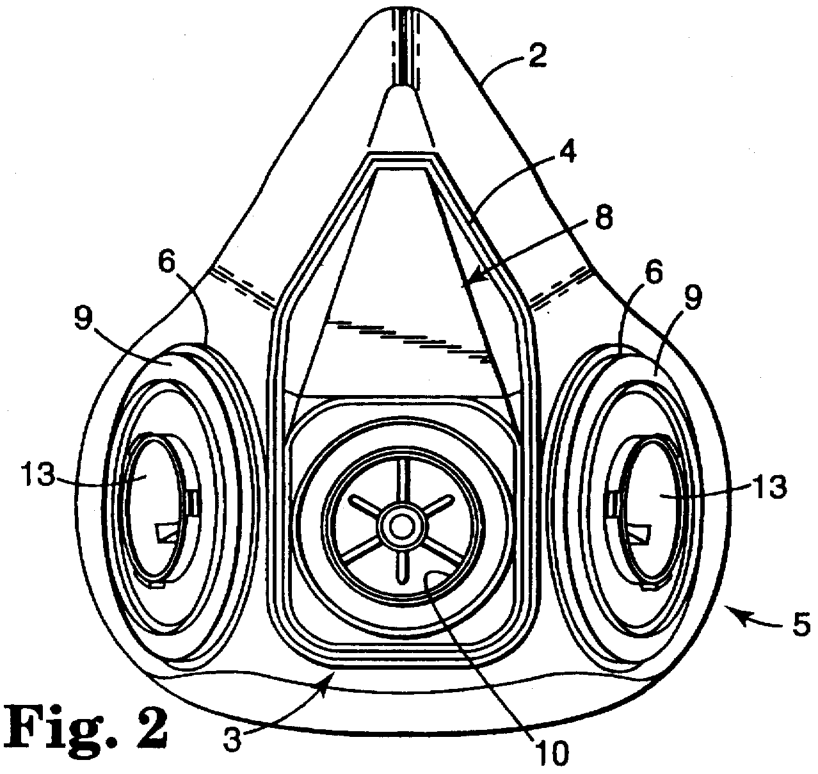
FIG. 2 is a front view of the facepiece of the mask shown in FIG. 1.

The mask 1 shown in FIG. 1 is a half mask, that is, it is intended to fit over the nose, mouth and chin of the wearer. The mask comprises a facepiece 2, best seen in FIG. 2, which is formed from a soft, compliant material (for example, a rubber material) and has an inturned cuff (not visible) around its edge, which will form a seal against the wearer's skin. The facepiece 2 comprises a central portion 3 containing a nose opening 4, and two swept-back side portions 5 each containing a cheek opening 6. The mask also comprises a rigid insert which is positioned against, and sealed to, the rear side of the facepiece 2 and which provides the mask with nose and cheek portions 8 and 9, respectively, in the nose and cheek openings 4, 6.

The central part of the nose portion 8 is substantially flat and contains a nose aperture 10 which houses an exhalation valve (not visible). A valve cap 11 (FIG. 1), to which adjustable straps 12 are attached, is clipped over the nose aperture 10. Each cheek portion 9 contains a cheek aperture 13 which houses an inhalation valve (also not visible) and provides a bayonet fitting 15 for a filter cartridge 14 (FIG. 1). Alternatively, an air supply line (not shown) can be connected to the cheek apertures 13, in place of the filter cartridges 14.

In use, the straps 12 are adjusted to fit the head of the wearer and to hold the mask 1 against the wearer's face. If the mask is fitted with filter cartridges 14, as shown in FIG. 1, filtered air is drawn into the mask through the inhalation valves in the cheek apertures 13 when the wearer breathes in, and exhaled air is expelled through the exhalation valve in the nose aperture 10 when the wearer breathes out. That mode of use is known as "the filtering mode". If the mask is attached to an air supply line, a supply of clean air is fed continuously from the line into the mask through the inhalation valves in the cheek apertures 13. Only some of that air will be inhaled by the wearer, with the result that unused (excess) clean air will be expelled along with exhaled air through the exhalation valve in the nose aperture 10. That mode of use is known as "the supplied air mode".

Masks of the type shown in FIG. 1 are available from the 3M Company of St. Paul, Minn., U.S.A. under the product description "6000 Series Half Mask".

Figure 3:
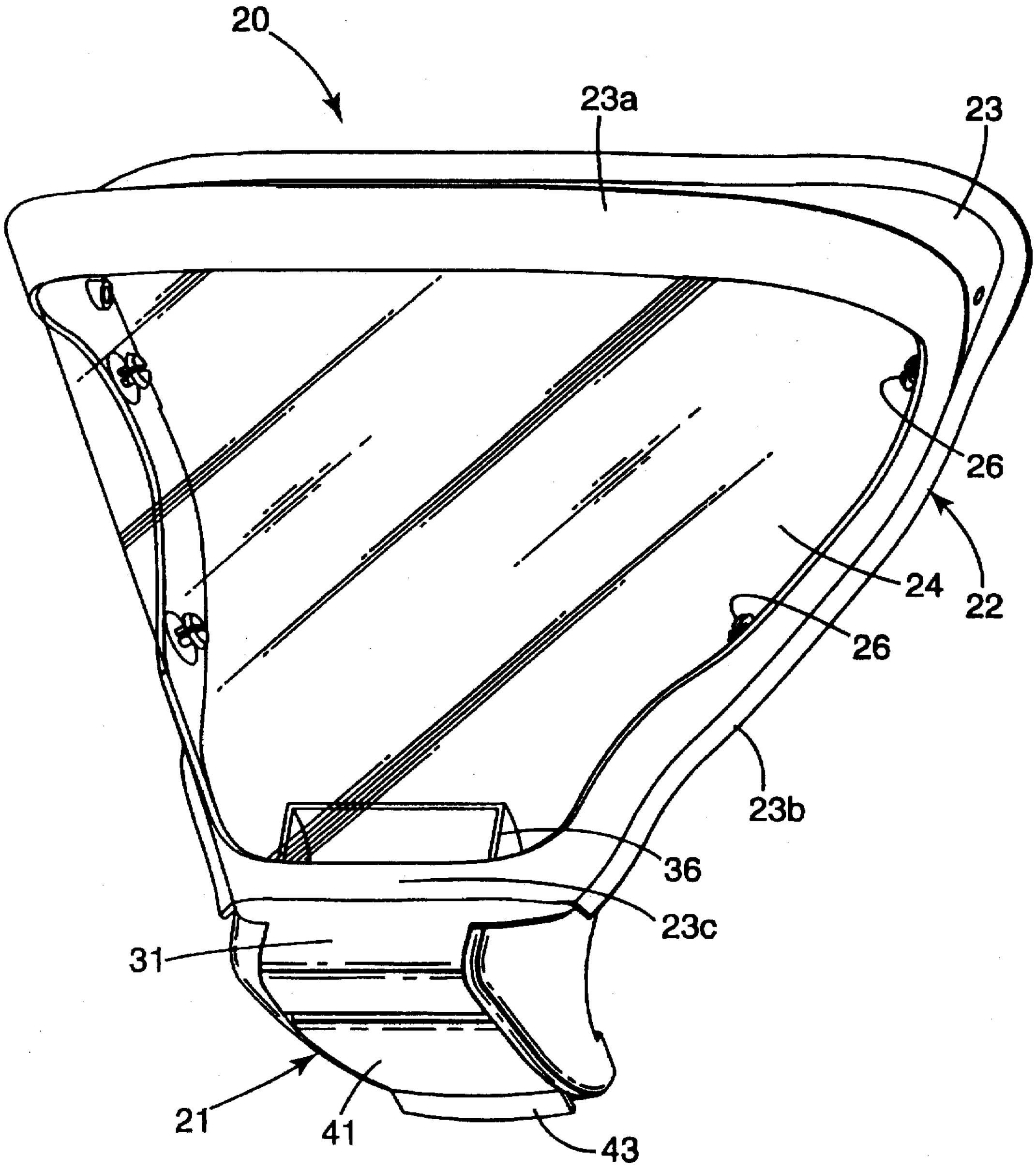
FIG. 3 is a perspective view (generally in the same direction as FIG. 1) of an eye shield for use with the mask shown in FIG. 1.
Figure 4:
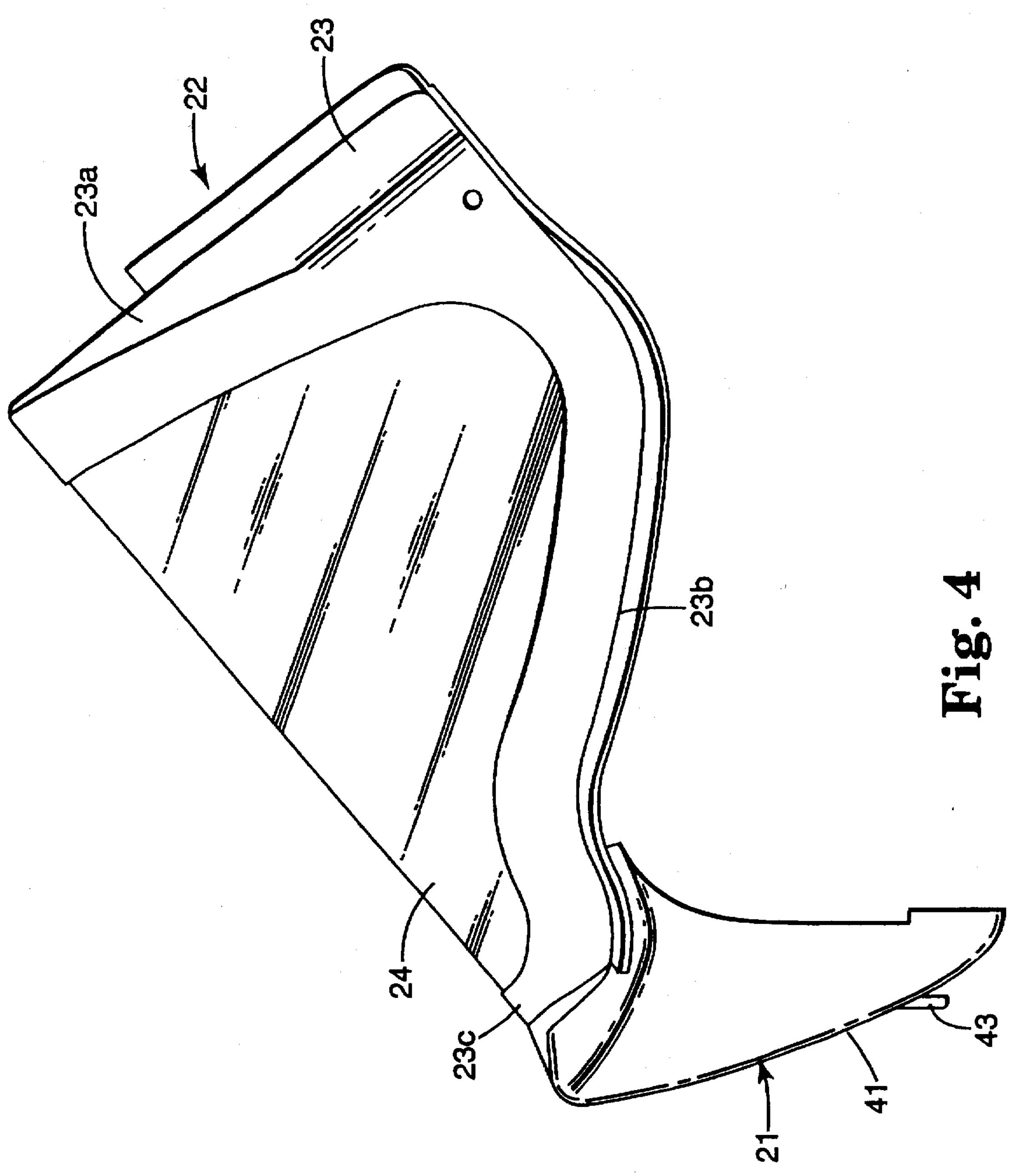
FIG. 4 is a side view of the eye shield shown in FIG. 3.
Figure 5:
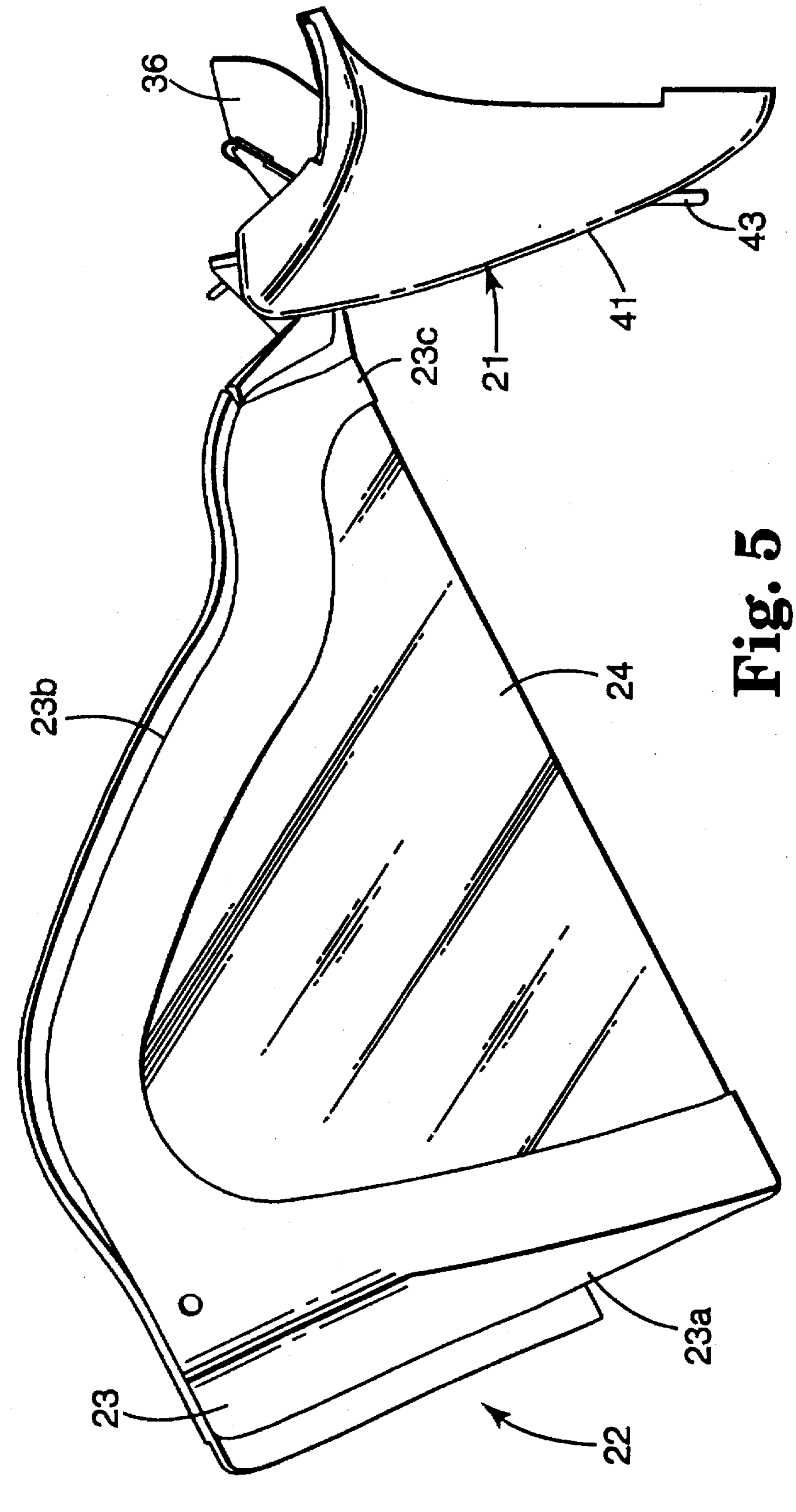
FIG. 5 is a side view of the eye shield in the same direction as FIG. 4 but showing the frame portion of the shield being moved to its lowered position.
Figure 6:
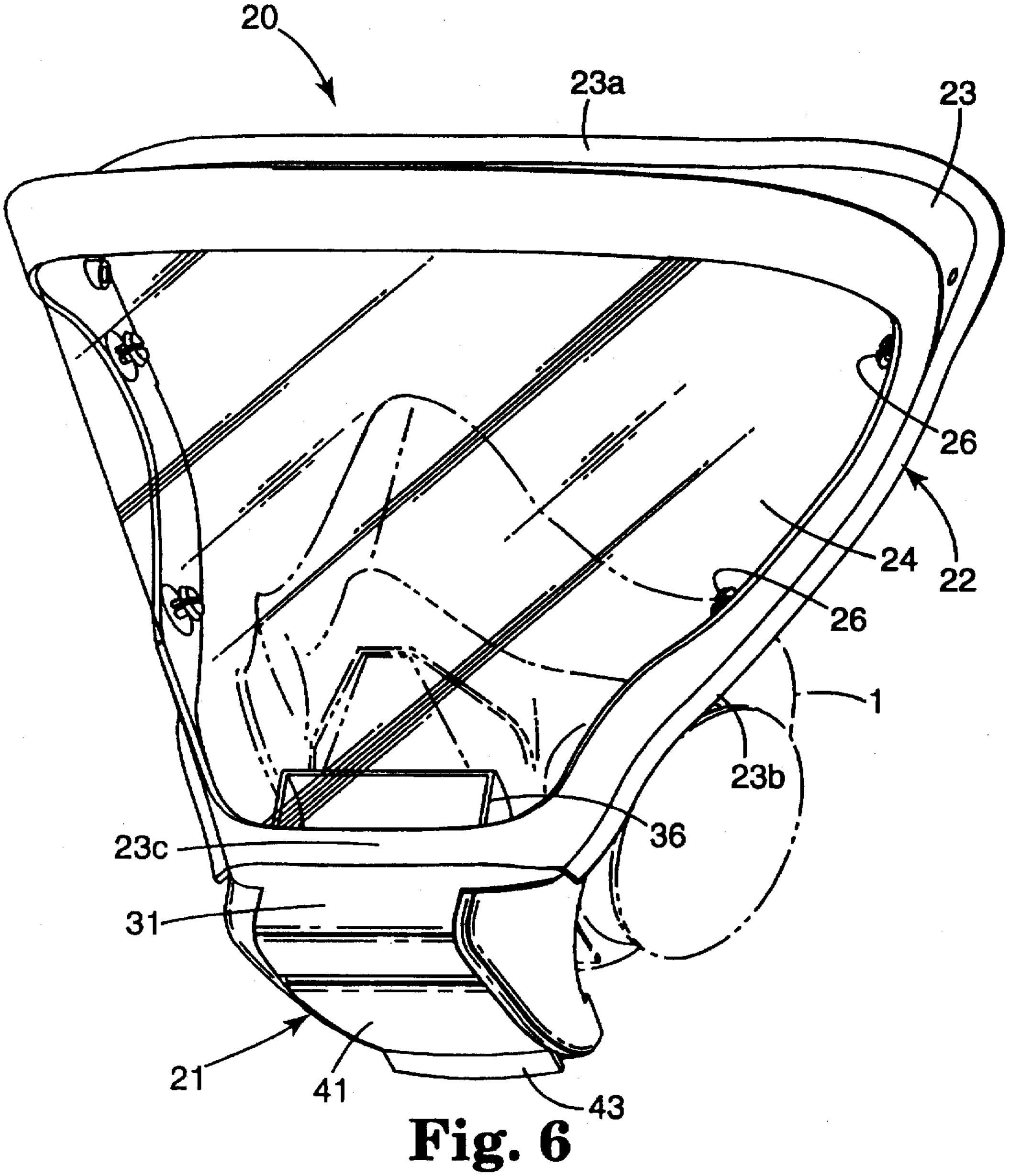
FIG. 6 is a perspective view (generally in the same direction as FIGS. 1 and 3) showing the eye shield attached to the mask of FIG. 1.

FIGS. 3 and 4 show an eye shield 20 which can be used with the mask shown in FIG. 1 when it is required to provide protection for the eyes, as well as the respiratory system, of the wearer. The eye shield comprises a body portion 21 which can be clipped over the valve cap 11 on the mask, and a shield portion 22 which is pivotally attached to the body portion so that it can be rotated forwards, as indicated in FIG. 5, into a lowered position. FIG. 6 shows the eye shield 20 mounted on the mask 1, with the shield portion 22 in the raised position, from which it will be appreciated that movement of the shield portion 22 into the lowered position will take the shield portion out of the line of vision of the wearer without affecting the respiratory protection provided by the mask. As seen in FIG. 6, the raised portion extends across a wear's forward line of vision. The manner in which the body portion 21 is attached to the mask, and the pivotal mounting of the shield portion 22, will be described in greater detail below.

The shield portion 22 comprises a frame 23 containing the lens 24 of the eye shield, and is shaped so that it will extend across the forehead and around the sides of the face of the wearer to shield the eyes without impeding the wearer's vision. To that end, the upper edge **23*a* of the frame 23 is curved to follow approximately the line of the wearer's forehead from one temple to the other, and the sides 23*b* of the frame curve back from the body portion 21 of the eye shield, to pass behind the wearer's eyes and join the upper edge of the frame at its outer ends. FIG. 6 shows how the sides 23*b* of the frame are also shaped to pass above the cheek portions 9 at the sides of the mask 1. The frame 23 is thus generally triangular in shape, with the base of the triangle intended to be located at the forehead of the wearer and the apex of the triangle in the nose region, while the sides of the triangle turn back around the sides of the wearer's face. The frame 23** is not intended to fit against the face of the wearer and it is self-supporting so that, once attached to the mask, no further means is required to secure it to the head of the wearer. The frame can be formed from any suitable material (preferably one that is solvent resistant) including polyamides, for example nylon; polyesters, for example PET; and polyolefines. The frame may be a moulded component but could also be cast or thermoformed.

Figure 8:
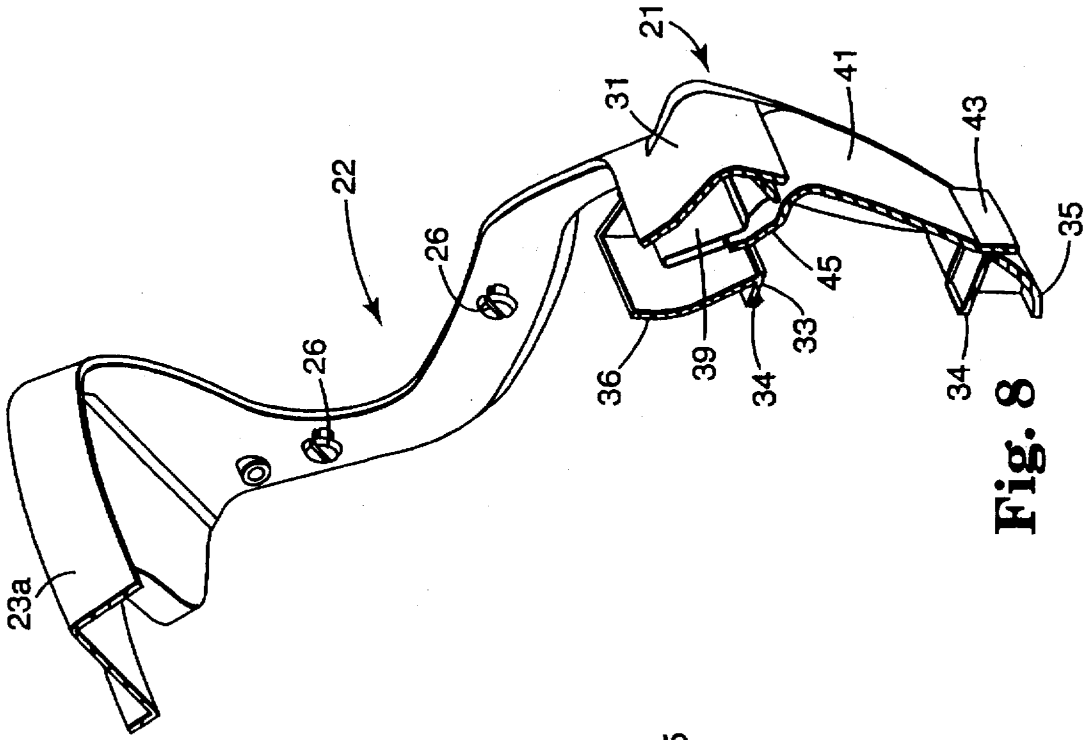
FIG. 8 is a perspective view, broken away, showing the inside of the frame and the body portion of the eye shield.
Figure 7:
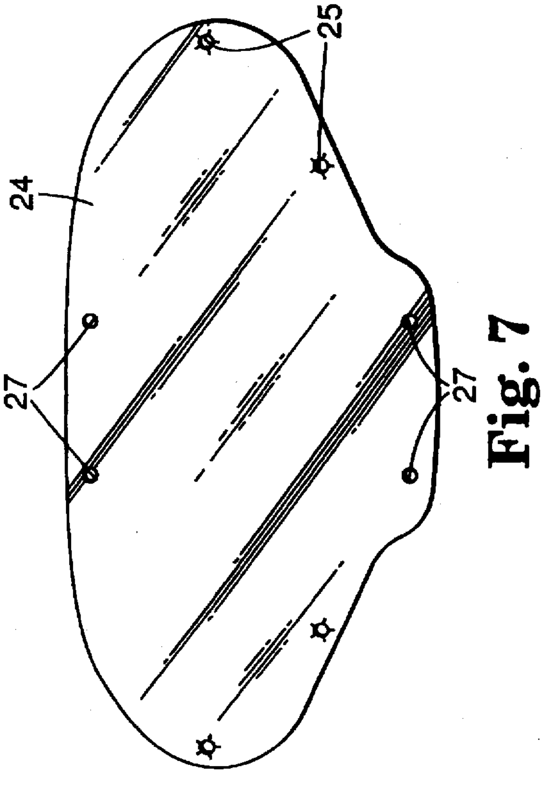
FIG. 7 is a view of the lens of the eye shield, removed from the frame.

The lens 24 comprises a flat sheet of a flexible, transparent film material which is secured in the frame 23 at the sides **23*b* and at the upper and lower edges 23*a*, 23*c* so that it adopts the curvature of the upper edge 23*a* around the face of the wearer (at a sufficient distance from the face to allow, for example, for spectacles to be worn). The lens sheet 24, which is shown in FIG. 7 removed from the eye shield, is generally triangular in shape to correspond to the shape of the frame 23 and has openings 25 in its side edge portions, in positions which correspond to those of fixing heads 26 on the sides 23*b* of the frame, and openings 27 in its upper and lower edge portions, in positions which correspond to those of locating posts 28 on the upper and lower edges 23*a*, 23*c* of the frame. The locating posts on the lower edge 23*c* of the frame do not appear in the drawings. The fixing heads 26, which are shown more clearly in FIG. 8, are generally mushroom-shaped and the corresponding openings 25 in the lens sheet 24 are provided with radially-extending slits which enable them to be pushed over the fixing heads. The locating posts 28, on the other hand, have a circular cross-section and the corresponding openings 27 in the lens sheet 24 are simply circular holes. Bands 29*a*, 29*c* (which, for clarity, are shown only in FIG. 10) are pivotally mounted on the inside of the upper and lower edges 23*a*, 23*c* of the frame, and cooperate with the locating posts 28 to secure the lens sheet 24** in position as will be described below.

To insert the lens sheet 24 into the frame 23, the bands **29*a*, 29*c* are first rotated away from the frame to expose the posts 28. The lens sheet 24 is then positioned in the frame so that the posts 28 are located in the openings 27 and the fixing heads 26 are pushed into the openings 25 whereupon the lens sheet will adopt the curvature of the upper frame edge 23*a*. The bands 29*a*, 29*c* are then rotated back towards the frame so that they lie along the upper and lower edges 23*a*, 23*c* and engage the posts 28**, thereby trapping the lens sheet in the frame. The lens sheet can be removed from the frame by carrying out the same steps in the reverse order.

The sheet 24 is formed by die cutting from a sheet of suitable eye-shielding material, for example a polyester or polycarbonate material, and, as described above, can easily be removed from the frame 23 and replaced by a new sheet if it should become marked during use. The sheet 24 should be able to withstand a certain amount of impact but should also be capable of adopting the curvature of the frame 23.

Figure 10:
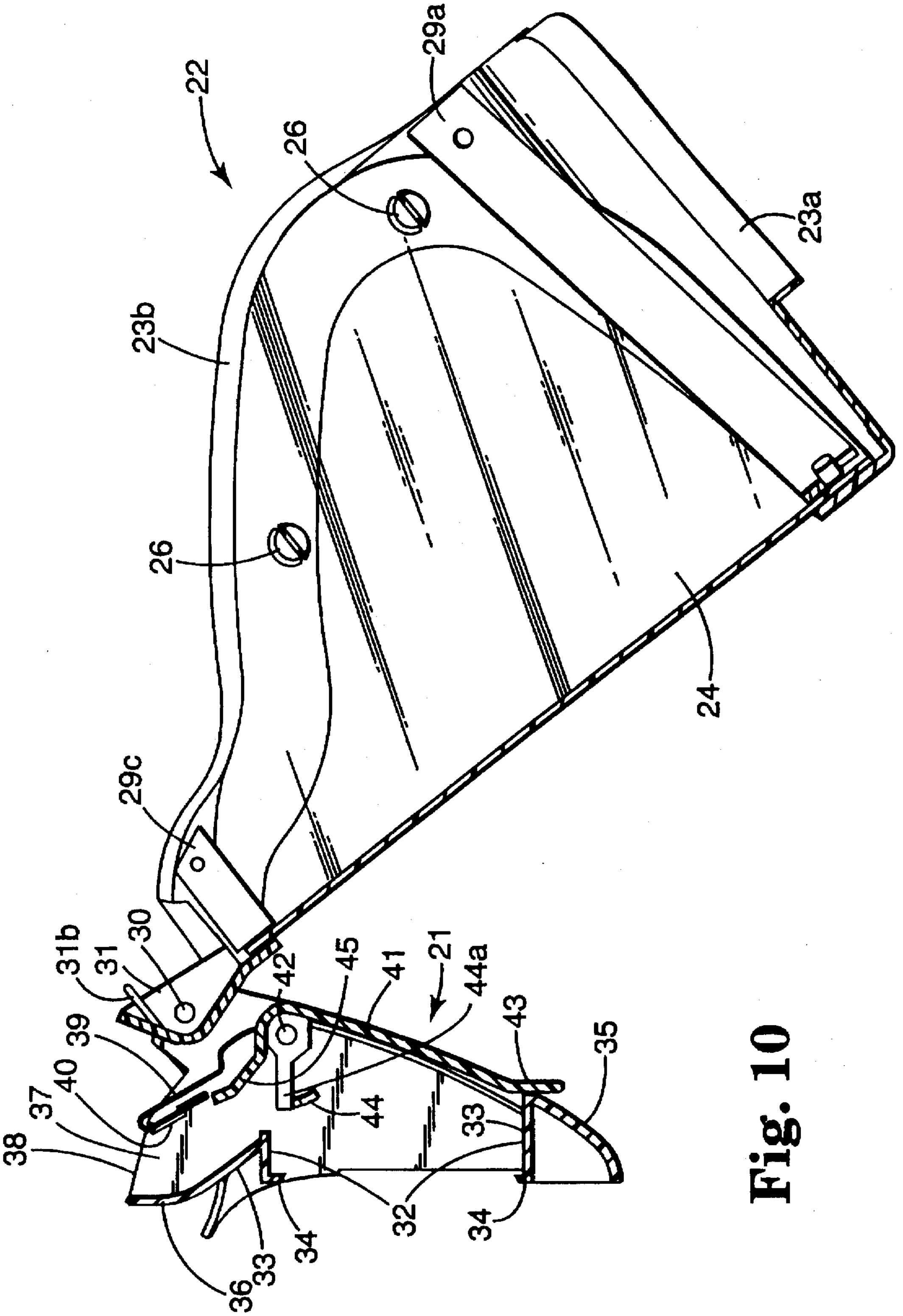
FIG. 10 is a cross-section through the eye shield as it is shown in FIG. 5, but viewed from the other side.
Figure 11:
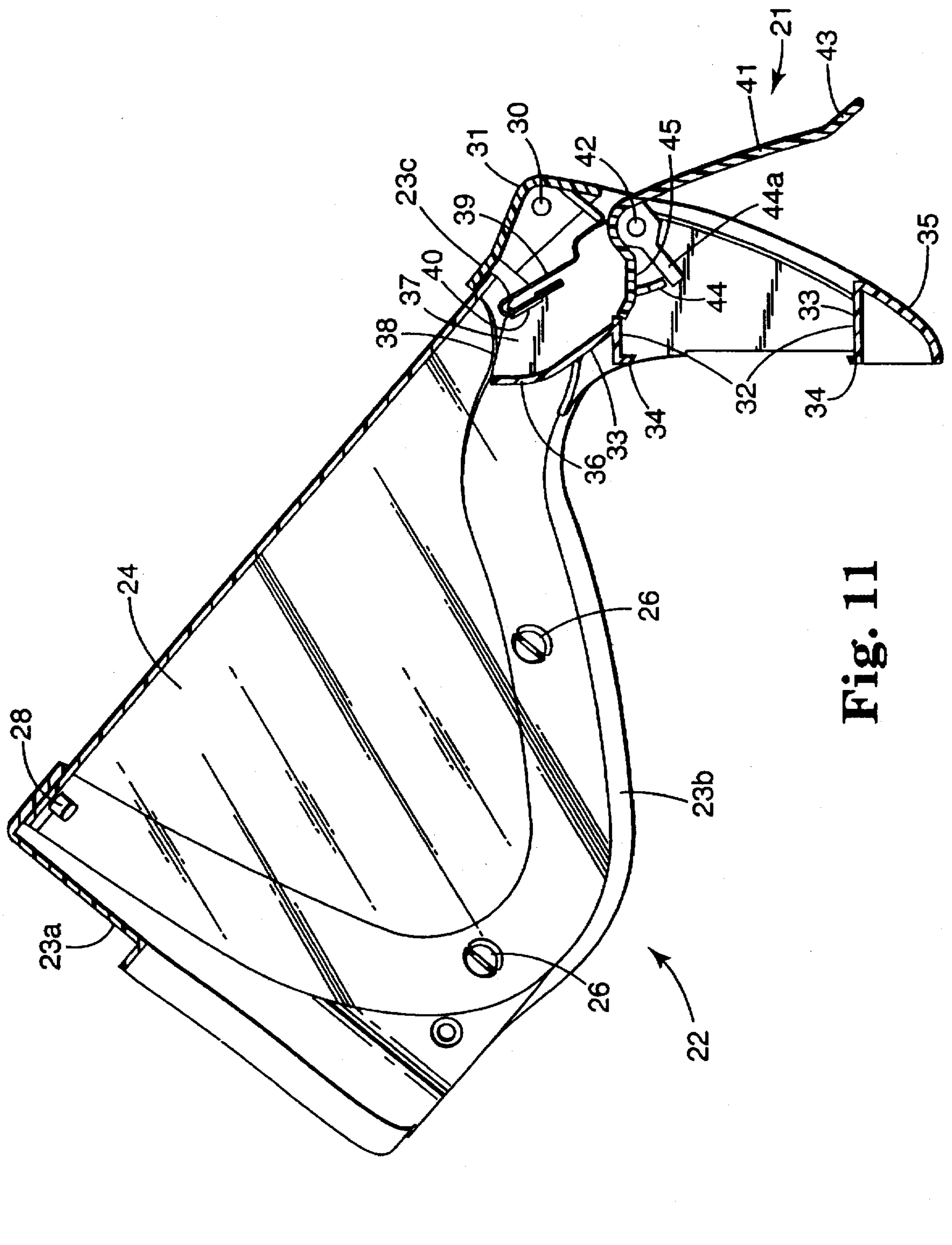
FIG. 11 is a view similar to that of FIG. 9, but showing a valve flap in an alternative position.
Figure 12:
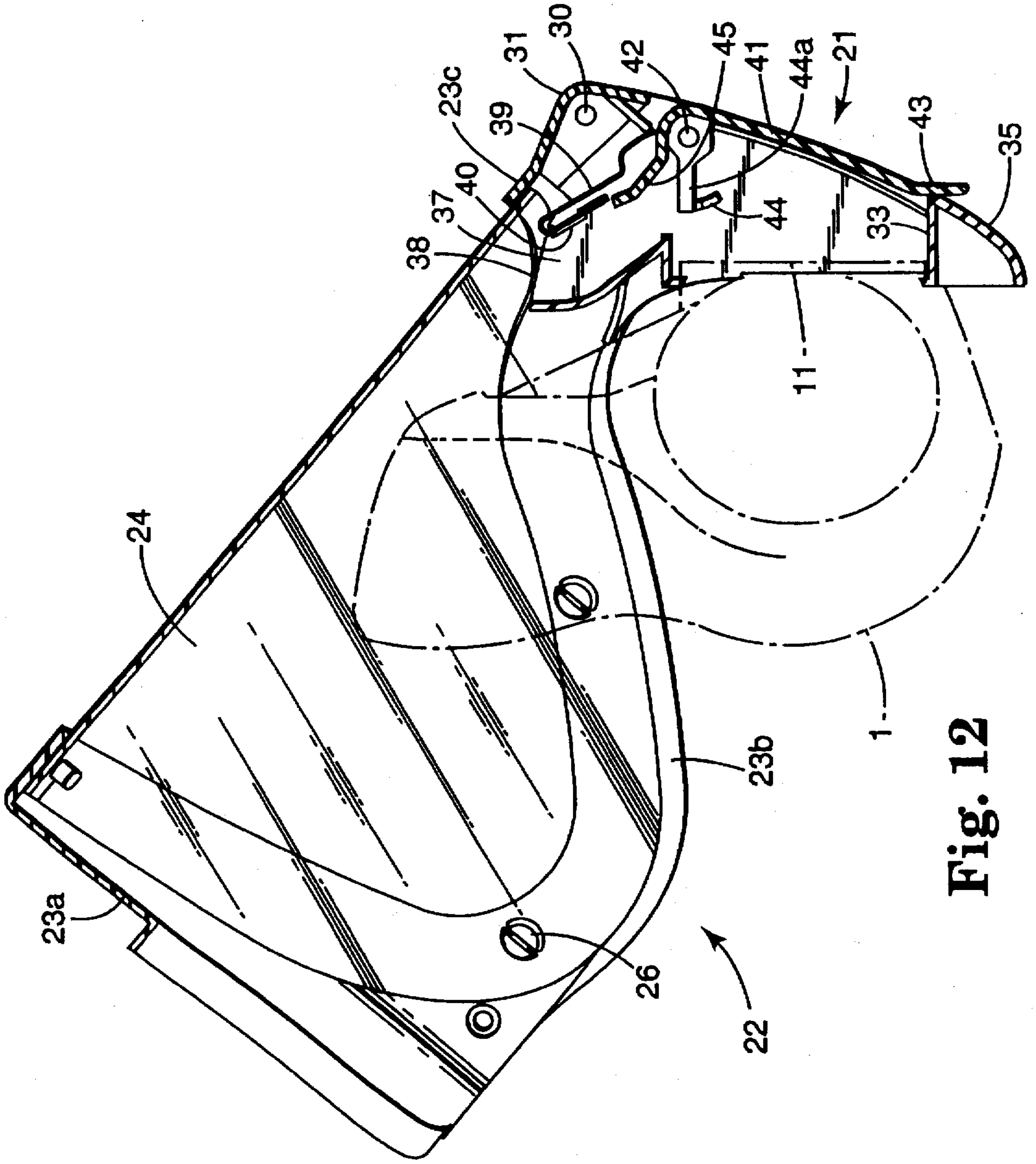
FIG. 12 is a cross-section similar to FIG. 9, through the eye shield attached to the mask.

As already mentioned, the shield portion 22 of the eye shield is pivotally attached to the body portion 21 so that it can be pivoted forwards, relative to the body portion, as shown in FIG. 5. When the eye shield is attached to a mask that is being worn, that movement will take the shield portion 22 below the forward line of vision of the wearer as seen in FIG. 10, but will not affect the respiratory protection provided by the mask: it allows the wearer to remove the eye protection temporarily, for example to inspect some work that is being carded out, without also removing the respiratory protection. The pivotal mounting 30 of the shield portion 22 is located in the upper end of the body portion 21, and in the side walls **31*a* of a lower extension 31 of the frame 23, and it allows the shield portion to be pivoted forwards until it hangs freely under gravity (i.e., substantially vertically downwards) from the body portion. In such a position, the shield portion is less likely to pull the mask 1** away from the face of the wearer.

The body portion 21 of the eye shield will now be described with reference, in particular, to FIGS. 9 to 12. The body portion is a molded item formed, typically, from a material similar to that of the frame 23 and is shaped to fit onto the nose portion 8 of the mask and, in particular, to clip on to the valve cap 11. The clips 32, which can be seen in FIGS. 9 to 12, comprise rearwardly-extending surfaces 33 formed as part of the molded body portion 21, which extend over the top and bottom of the valve cap 11 (shown in FIG. 12) and have lips 34 which engage behind the valve cap to hold the eye shield firmly on the mask. The eye shield 20 is then positively engaged with the mask 1 and will not, for example, tilt or rotate relative to the mask while it is being worn. The lower surface 33 has a curved surface 35 extending downwards from it, at the front of the body portion, such that forward pressure on the surface 35 will cause the surface 33 to deflect slightly to move the associated lip 34 out from behind the valve cap 11 when it is desired to remove the eye shield from the mask.

A rear surface 36 of the body portion 21 defines a passageway 37 which, when the eye shield 20 is attached to the mask, leads from the space inside the body portion immediately in front of the valve cap 11 to an outlet 38 at the top of the body portion on the rear side of the transparent sheet 24. The purpose of the passageway 37 will be described below.

Figure 9:
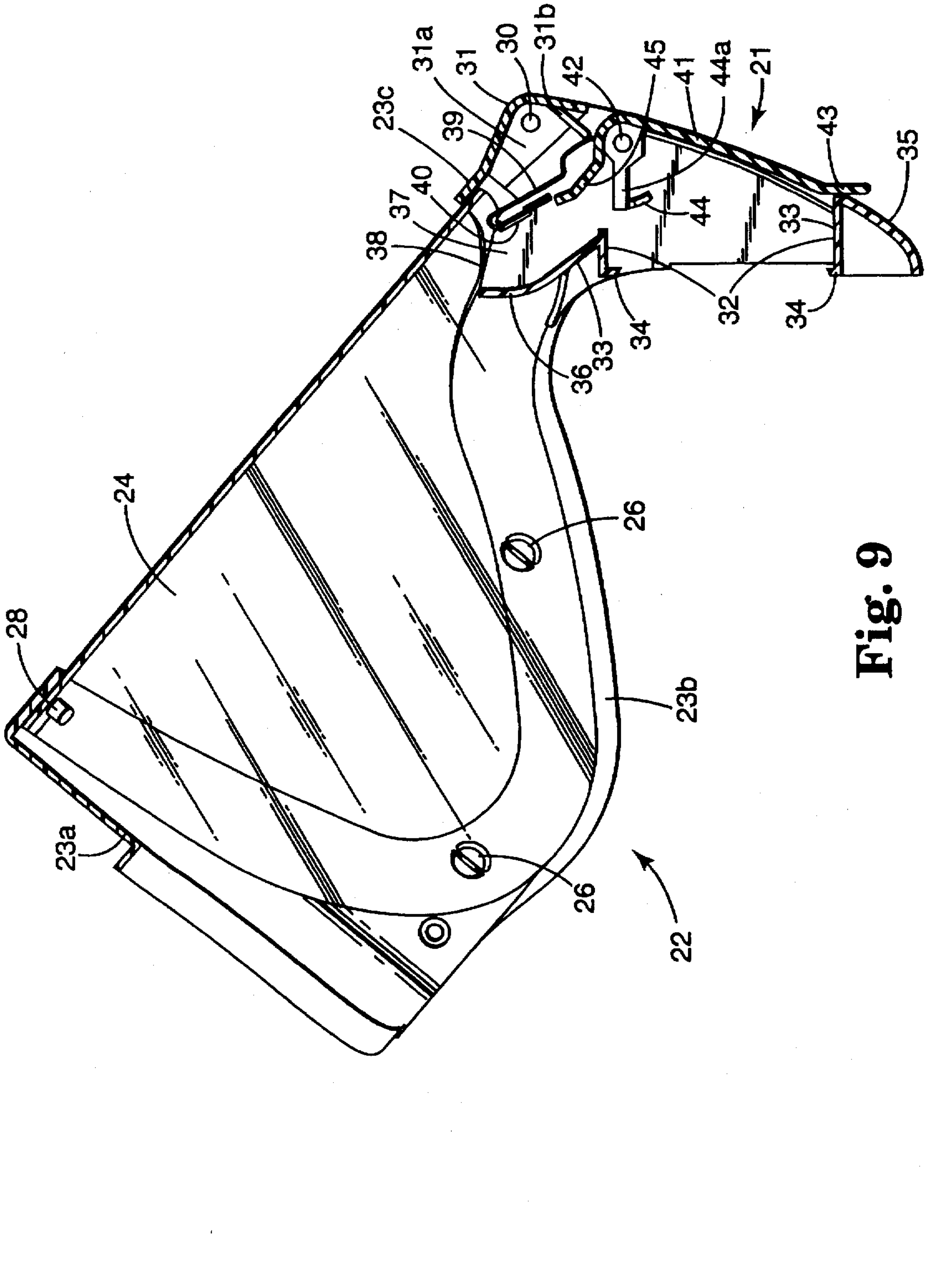
FIG. 9 is a cross-section through the eye shield as it is shown in FIG. 4, but viewed from the other side.

Also within the body portion 21 is a leaf spring 39 which is associated with the lower frame extension 31 of the shield portion 22. The leaf spring 39 extends across the width of the passageway 37 within the body portion and is held at each end in slits 40 in side walls of the passageway. When the shield portion is in the raised position, the leaf spring 39 contacts on portion **31*b* of the frame extension 31, as shown in FIG. 9, and biases the frame in the direction of the face of the person wearing the mask, thereby ensuring that the shield is held in position even if the wearer bends over. In addition, the bias ensures that the upper edge 25 of the frame 23 always rests against the forehead of the wearer, which thus provides a reference point ensuring correct location of the shield relative to the wearer's face. A foam strip (not shown) can be provided on the inside of the upper edge 25 of the frame, in the region of contact with the wearer's face. When the shield portion 22 is in the lowered position, on the other hand, portion 31i b l of the frame extension 31 moves out of contact with the leaf spring 39, as shown in FIG. 10**, leaving the shield portion unbiased and free to accommodate the wearer's movements.

The from of the body portion 21, immediately in front of the valve cap 11, is formed by a valve flap 41 which is pivotally-mounted at 42 in the body portion so that it can be rotated about its upper edge between a closed position (shown in FIG. 9) and an open position (shown in FIG. 11) in which the flap extends out from the body portion. A projecting portion 43 is provided on the lower edge of the valve flap 41 to assist the mask wearer in moving the flap. Upstanding ramp-shaped surfaces 44 on side walls of the body portion 21, one on each side of the valve flap 41, cooperate with legs **44*a* on the valve flap and cause the legs 44*a* to deflect as the valve flap is moved between the open and closed positions, thereby ensuring that the valve flap is not free to swing when in either the open or the closed position and requires a positive force to move it between those positions. A closure surface 45 is formed at the top of the valve flap and extends inwards from the top of the flap into the body portion 21 and towards the passageway 37. When the valve flap 41 is moved to the open position (FIG. 11 ), the closure surface 45 extends across, and closes, the passageway 37 but, when the valve flap 41 is in the closed position (FIG. 9), the passageway 37** is open.

When the passageway 37 is open (i.e., the valve flap 41 is in the closed position), air that leaves the mask 1 through the exhalation valve in the nose aperture 10 will be diverted by the flap 41 along the passageway 37 and into the region on the inside of the transparent sheet 24. The rear surface 36 of the passageway is shaped adjacent the outlet 38 to act as a deflector, ensuring that the air leaving the outlet is not directed at the eyes of the wearer but passes instead over the inside surface of the lens sheet 24. That mode of operation is used when the mask is being used in the supplied air mode, when the air leaving the mask is composed mainly of excess clean air. The excess clean air then serves to remove contaminants from the region of the wearer's eyes as it passes behind the lens sheet 24, thus providing protection for the eyes against mists and vapours, and it will also serve to prevent the sheet 24 from misting over and to cool the wearer. The air leaves the eye shield through the spaces between the frame 23 and the wearer's face.

When the passageway 37 is closed (i.e., the valve flap 41 is in the open position), air that leaves the mask 1 through the exhalation valve in the nose aperture will leave the body portion of the eye shield directly through the opening of the valve flap 41. That mode of operation is used when the mask is being used in the filtering mode, when the air leaving the mask is exhaled air. It could, however, also be used when the mask is being used in the supplied air mode and the wearer does not need clean air to be fed into the region behind the lens sheet 24.

An eye shield of the type described above and shown in the drawings offers the advantage that it can be used with an available type of half mask, and could readily be adapted for use with other, similar, half masks by modifying the shaping of the body portion 21. The eye shield is easily secured to, and removed from, a mask and does not require the mask to be modified in any way. In addition, the lens sheet 24 is easily replaced in the event that it becomes marked. The eye shield not only allows the wearer to move the shield portion 22 out of the line of vision without removing the mask, so that respiratory protection is always maintained, but also offers the possibility of effective eye protection when the mask is used in the supplied air mode by using air from the mask to remove contaminants from the region of the wearer's eyes.

It will be appreciated that, although the eye shield described above and shown in the drawings has a number of advantageous features, not all of those features need be provided together. For example, it may not always be necessary to be able to lower the shield portion 22 out of the line of vision of the wearer, in which case the pivotal mounting of the shield portion on the body portion 21 could be omitted. In some cases, the circulation of air over the inside surface of the lens sheet 24 might always be required, in which case the valve flap 41 at the front of the body portion could be permanently closed. Alternatively, the circulation of air over the inside surface of the lens sheet 24 may never be required, in which case the valve flap 41 could be omitted completely.

There are also other modifications that could be made to the eye shield described above and shown in the drawings. For example, although it is straightforward to replace the lens sheet 24 when it becomes marked, it would be possible to protect the sheet with a film cover which can be peeled away. In certain circumstances, the frame 23 for containing the sheet 24 may not be required: in that case, a simple rectangular piece of sheet material could be used instead of the shaped sheet 24. When the frame 23 is used, any suitable arrangement can be employed for securing the sheet 24 in the frame. For example, additional mushroom-shaped fixing heads (similar to the heads 26) could be provided on the upper and lower edges 23*a*, 23*c* of the frame instead of the locating posts 28 and bands 29*a*, 29*c*. Alternatively, slots could be provided in the upper and lower edges of the frame, to receive the upper and lower edge portions of the lens sheet. As a further alternative, the lens sheet 24 could be located in the frame 23 by means of a suitable peelable adhesive.

It is also not essential for the eye shield to be attached to the valve cap 11 of the mask: if the body portion 21 were extended sideways, the eye shield could, for example, be attached to the mask at the cheek portions 9 using a filter cartridge 14 to secure it in place. Alternatively, the mask straps 12 could be used as attachment points for the eye shield. When the valve cap 11 is used as the attachment location, it could be formed as an integral part of the body portion 21 of the eye shield rather than as a separate component. Moreover, it is not essential for the eye shield to be attached to the mask by clips as described: any appropriate means of attachment could be used including, for example, adhesive strips or hook-and-loop fastenings.

The pivotal mounting of the shield portion 22 of the eye shield need not be located at the top of the body portion 21, although that is a particularly convenient location because it allows the shield portion to hang vertically downwards when it is in the lowered position without being directly adjacent the body of the wearer. The shield portion 22 could, as an alternative, be mounted on the lower part of the body portion 21 but would then hang lower, and closer to the body of the wearer. It is also not essential for the shield portion 22 to be mounted on pivots on the body portion 21 as illustrated: it could, as an alternative, be hinged to the body portion.

The diverter valve flap 41 and associated closure surface 45 could be replaced by any other suitable valve arrangement that would function to direct air from the mask either to the eye region of the wearer or the atmosphere. As a further modification, the valve flap 41 (or alternative valve arrangement) could have one or more intermediate positions in which only some of the air from the mask is directed to the eye region of the wearer and the rest is directed to atmosphere. In some cases, it may be desirable that the valve arrangement never directs all of the air from the mask to the eye region of the wearer but always allows some of that air to escape to atmosphere.

It will also be appreciated that use of an eye shield of the type described above and shown in the drawings is not restricted to half masks. An eye shield of the type described could be used with a full face mask, either to provide additional protection for the wearer (for example, against ultraviolet radiation) or to provide inexpensive and disposable protection for the mask.

We claim:

1. An eye shield for use in combination with a respiratory mask which is adapted to fit to, and seal against, the face of a wearer, the eye shield comprising an eye-shielding portion, and attachment means by which the eye shield can be releasably secured to the mask in positive engagement therewith and positioned to shield the eyes of a wearer without, in use, requiring means for securing the eye shield to the head of the wearer, a body portion in which the attachment means is formed and to which the eye shielding portion is attached, pivot means for pivotally attaching said eye shielding portion to said body portion between a first position in which the eye shielding portion extends across a wearer's forward line of vision and a second position in which said eye shielding portion extends below the wearer's forward line of vision.

2. An eye shield as claimed in claim 1, including resilient means arranged to bias the eye-shielding portion in the direction of the face of the wearer when the eye-shielding portion is in the first position.

3. An eye shield for use in combination with a respiratory mask which is adapted to fit to, and seal against, the face of a wearer, the eye shield comprising an eye-shielding portion, a valve means having a diverter position in which, when the eye shield is secured to the mask, the valve means diverts air that has left the mask to the interior of the eye shield and attachment means by which the eye shield can be releasably-secured to the mask in positive engagement therewith and positioned to shield the eyes of a wearer without, in use, requiring means for directly securing the eye shield to the head of the wearer.

4. An eye shield for use in combination with a respiratory mask which is adapted to fit to, and seal against, the face of a wearer, the eye shield comprising an eye-shielding portion, a valve means having a diverter position in which when the eye shield is secured to the mask, the valve means diverts air that has left the mask to the interior of the eye shield and a deflector which is so arranged that, when the valve means is in the diverter position, air that has left the mask is directed by the deflector over the internal surface of the eye-shielding portion and attachment means by which the eye shield can be releasably-secured to the mask in positive engagement therewith and positioned to shield the eyes of a wearer without, in use, requiring means for directly securing the eye shield to the head of the wearer.

5. An eye shield for use in combination with a respiratory mask which is adapted to fit to, and seal against, the face of a wearer, the eye shield comprising an eye-shielding portion, a valve means having a diverter position in which, when the eye shield is secured to the mask, the valve means diverts air that has left the mask to the interior of the eye shield, the valve means having at least one position in which at least some of the air that has left the mask is directed outside the eye shield and attachment means by which the eye shield can be releasably-secured to the mask in positive engagement therewith and positioned to shield the eyes of a wearer without, in use, requiring means for directly securing the eye shield to the head of the wearer.

* * * * *

UNITED STATES PATENT AND TRADEMARK OFFICE

CERTIFICATE OF CORRECTION

PATENT NO.: 5,689,833

DATED: November 25, 1997

INVENTOR(S): Peter B. Allen, David Cook, and William A. Mittelstadt

It is certified that error appears in the above-identified patent and that said Letters Patent is hereby corrected as shown below:

On the Title page, item [56],
Under the subheading of "U.S. PATENT DOCUMENTS" of heading "References Cited" insert
--5,191,882 (equivalent of EPO 0 386 605 B1) 3/1993 Vogliano 128/207.11--

On the Title page, item [56],
Under the subheading of "FOREIGN PATENT DOCUMENTS" of heading "References Cited" insert
--0 386 605 B1 9/1990 Europe--
0 091 647 A1 10/1983 Europe
WO 89/10106 11/1989 WIPO--.

Column 1, line 41: Delete the work "carded" and insert in place thereof --carried--.

Column 1, line 50: After the word "use" insert --.--.

Column 3, line 42: After the word "raised" insert --position of the shield--.

Column 4, line 57: Delete the word "carded" and insert in place thereof --carried--.

Column 5, line 42: Delete "31i b l" and insert in place thereof --31b--.

Column 5, line 46: After the word "The", delete the word "from" and insert in place thereof --front--.

Signed and Sealed this

Twelfth Day of May, 1998

Attest:

BRUCE LEHMAN

*Attesting Officer* *Commissioner of Patents and Trademarks*

UNITED STATES PATENT AND TRADEMARK OFFICE

CERTIFICATE OF CORRECTION

PATENT NO.: 5,689,833

DATED: November 25, 1997

INVENTOR(S): Peter B. Allen, David Cook, and William A. Mittelstadt

It is certified that error appears in the above-identified patent and that said Letters Patent is hereby corrected as shown below:

TITLE PAGE:

Under the subheading of "FOREIGN PATENT DOCUMENTS" of heading "References Cited" delete "42 20 790 C1" and insert in place thereof --42 20 780 C1--.

Signed and Sealed this

Seventh Day of July, 1998

Attest:

BRUCE LEHMAN

*Attesting Officer*

*Commissioner of Patents and Trademarks*